United States Patent
Hattori et al.

(10) Patent No.: US 6,812,012 B1
(45) Date of Patent: Nov. 2, 2004

(54) LUCIFERASE AND METHODS FOR ASSAYING INTRACELLULAR ATP BY USING THE SAME

(75) Inventors: Noriaki Hattori, Chiba (JP); Seiji Murakami, Chiba (JP)

(73) Assignee: Kikkoman Corporation, Noda (JP)

( * ) Notice: Subject to any disclaimer, the term of this patent is extended or adjusted under 35 U.S.C. 154(b) by 0 days.

(21) Appl. No.: 09/581,241

(22) PCT Filed: Dec. 24, 1998

(86) PCT No.: PCT/JP98/05864

§ 371 (c)(1),
(2), (4) Date: Jun. 26, 2000

(87) PCT Pub. No.: WO99/33997

PCT Pub. Date: Jul. 8, 1999

(30) Foreign Application Priority Data

Dec. 26, 1997 (JP) .............................. 9/361022

(51) Int. Cl.[7] .......................... C12N 9/02; C12N 1/21; C12N 5/16; C12N 15/52; C07H 21/04

(52) U.S. Cl. ............... 435/189; 435/252.3; 435/252.33; 435/254.11; 435/320.1; 435/325; 536/23.2

(58) Field of Search .............................. 435/189, 252.3, 435/252.33, 254.11, 320.1, 325, 8; 536/23.2

(56) References Cited

U.S. PATENT DOCUMENTS

| 5,229,285 A | 7/1993 | Kajiyama et al. ........... 438/189 |
| 6,074,859 A * | 6/2000 | Hirokawa et al. .......... 435/189 |

FOREIGN PATENT DOCUMENTS

| EP | 0 524 448 | 1/1993 |
| JP | 2-17189 | 7/1990 |
| JP | 5-244942 | 9/1993 |
| JP | 6-504200 | 5/1994 |
| JP | 7-203995 | 8/1995 |
| WO | WO 92/12253 | 7/1992 |
| WO | WO 96/07759 | 3/1996 |

OTHER PUBLICATIONS

Tatsumi et al. (1992) Biochimica & Biophysica Acta, vol. 1131, pp. 161–165.*

Simpson et al. (1991) Journal of Bioluminescence and Chemiluminescence, vol. 6, pp. 97–106.*

W. J. Simpson, et al., The Journal of Bioluminescence and Chemiluminescence, vol. 6, No. 2, pp. 97–106, "The Effect of Detergents on Firefly Luciferase Reactions", 1991.

H. Tatsumi, et al., Biochimica et Biophysica Acta, vol. 1131, pp. 161–165, "Molecular Cloning and Expression in *Escherichia coli* of a cDNA Clone Encoding Luciferase of a Firefly, Luciola Lateralis", 1992.

T. Masuda, et al., Gene, vol. 77, pp. 265–270, "Cloning and Sequence Analysis of cDNA for Lucifirase of a Japanese Firefly, *Luciola Cruciata*", 1988.

* cited by examiner

Primary Examiner—Elizabeth Slobodyansky
(74) Attorney, Agent, or Firm—Oblon, Spivak, McClelland, Maier & Neustadt, P.C.

(57) ABSTRACT

The present invention relates to luciferase having resistance to a surfactant and a method for measuring intracellular ATP which is characterized in that the luciferase having resistance to a surfactant is used in this method comprising the steps of: a first step wherein ATP is extracted from cells in a sample; a second step wherein light emission is produced by adding a luminescence reagent containing luciferase to the extracted ATP solution; and a third step wherein the light emission is measured.

21 Claims, 4 Drawing Sheets

LUCIFERASE AND METHODS FOR ASSAYING INTRACELLULAR ATP BY USING THE SAME

TECHNICAL FIELD

The present invention relates to novel luciferase having resistance to a surfactant and a method for measuring intracellular ATP using the same.

BACKGROUND ART

Intracellular ATP is routinely measured for determining the presence of cells in a sample or the number of cells in the fields of food sanitation, biology, clinical examinations, medical science, ultrapure water, and environmental science. A general method for measuring intracellular ATP comprises the steps of adding an ATP extraction reagent containing a surfactant as an effective component to a sample containing cells, extracting intracellular ATP, adding a luminescence reagent containing luciferase into the sample, and then measuring the total amount of light emitted.

Luciferase is an enzyme that catalyzes luminescence reaction of luciferin, which is a substrate, in the presence of ATP and magnesium ion. Luciferase used in a method for measuring intracellular ATP includes those derived from firefly species, such as GENJI firefly (*Luciola cruciata*), HEIKE firefly (*Luciola lateralis*), North American firefly and Russian firefly, etc.

Intracellular ATP can be extracted by adding an ATP extraction reagent to a sample containing cells and then stirring the sample.

To make full use of the capabilities of the extraction reagent, preferably the reaction agent is added so that the concentration of a surfactant becomes 0.05% or more of the mixture of the sample and the extraction reagent. However, a condition where the concentration of the surfactant is 0.05% or more, this inhibits significantly the enzyme reaction in the process of measuring ATP concentration by bioluminescence. Thus the sensitivity and accuracy of measurement are largely impaired. This is because a surfactant at such a high concentration lowers luciferase activity.

For example, North American firefly luciferase activity decreases to about 20% in the presence of 0.1% enzalkonium chloride (See Table 1).

On the other hand, inhibition of the bioluminescent reaction can be reduced with a lower concentration of surfactant. However, in this case the extraction efficiency for ATP would be insufficient.

A method wherein cyclodextrin or its derivative is used is a known method for suppressing the inhibition of luminescence reaction by a surfactant (Japanese Patent Application Laid-Open No. 6-504200).

Among methods for measuring intracellular ATP wherein intracellular ATP is extracted by allowing a sample to contact with a surfactant and subsequently ATP is measured by luciferin-luciferase bioluminescent reaction method, a method for measuring intracellular ATP characterized by the application of the bioluminescent reaction method after allowing a sample, from which ATP is extracted, to contact with cyclodextrin (Japanese Patent Application Laid-Open Publication No. 7-203995) is also known.

There has been no attempt so far to suppress the inhibition of bioluminescent reaction due to a surfactant focusing on luciferase.

The purpose of the invention is to provide a novel luciferase having anti-surfactant resistance, whose activity is not impaired by the presence of a surfactant at a high concentration. The other purpose of the invention is to provide a method, comprising the steps of extracting intracellular ATP using a surfactant and measuring intracellular ATP by bioluminescent reaction using a luciferase, which can lower the inhibition of bioluminescent reaction due to a surfactant without a decrease in efficiency in extracting intracellular ATP.

In the context of this specification, the term "suppress" is used to describe significant reduction of the inhibition of the luminescence reaction by a surfactant and the complete elimination of this inhibition.

DISCLOSURE OF THE INVENTION

The present invention relates to a luciferase having anti-surfactant resistance.

The luciferase having resistance to a surfactant includes a luciferase, wherein an amino acid at the 490-position, or an amino acid corresponding to the amino acid at 490-position of GENJI firefly or HEIKE firefly is substituted by an amino acid other than amino acid, e.g., lysine in the amino acid sequence of a wild-type firefly luciferase.

Further, the luciferase having resistance to a surfactant includes a polypeptide consisting of (a) or (b):
(a) A polypeptide consisting of the amino acid sequence shown in SEQ ID NO-4,
(b) A polypeptide comprising additions, deletions, or substitutions of one or more of amino acids in the polypeptide of (a), and having luciferase activity resistant to a surfactant, or
a polypeptide consisting of (a) or (b):
(a) A protein consisting of an amino acid sequence shown in SEQ ID NO:6,
(b) A protein comprising additions, deletions, or substitutions of one or more of amino acids in the polypeptide of (a), and having luciferase activity resistant to a surfactant.

Further, the present invention relates to a luceferase gene encoding the luciferase having resistance to a surfactant.

Furthermore, the present invention relates to a recombinant vector containing the luceiferase gene encoding the luciferase having resistance to a surfactant.

The present invention also relates to a transformant containing the recombinant vector.

In addition, the present invention relates to a method for producing the luciferase, comprising the steps of culturing the recombinant in a medium, and collecting luciferase with resistance to a surfactant from the culture product.

Moreover the present invention relates to a method for measuring intracellular ATP, comprising the steps of a first step wherein ATP is extracted in the presence of a surfactant from cells in a sample; a second step wherein a luminescence reagent containing luciferase is added to the extracted ATP solution so as to cause light emission; and a third step wherein the light emission is measured, and characterized in that luciferase having resistance to a surfactant is used.

This specification encompasses the description and/or drawings given in Japanese Patent Application No. H09-361022.

DETAILED DESCRIPTION OF THE INVENTION

Figure 1:
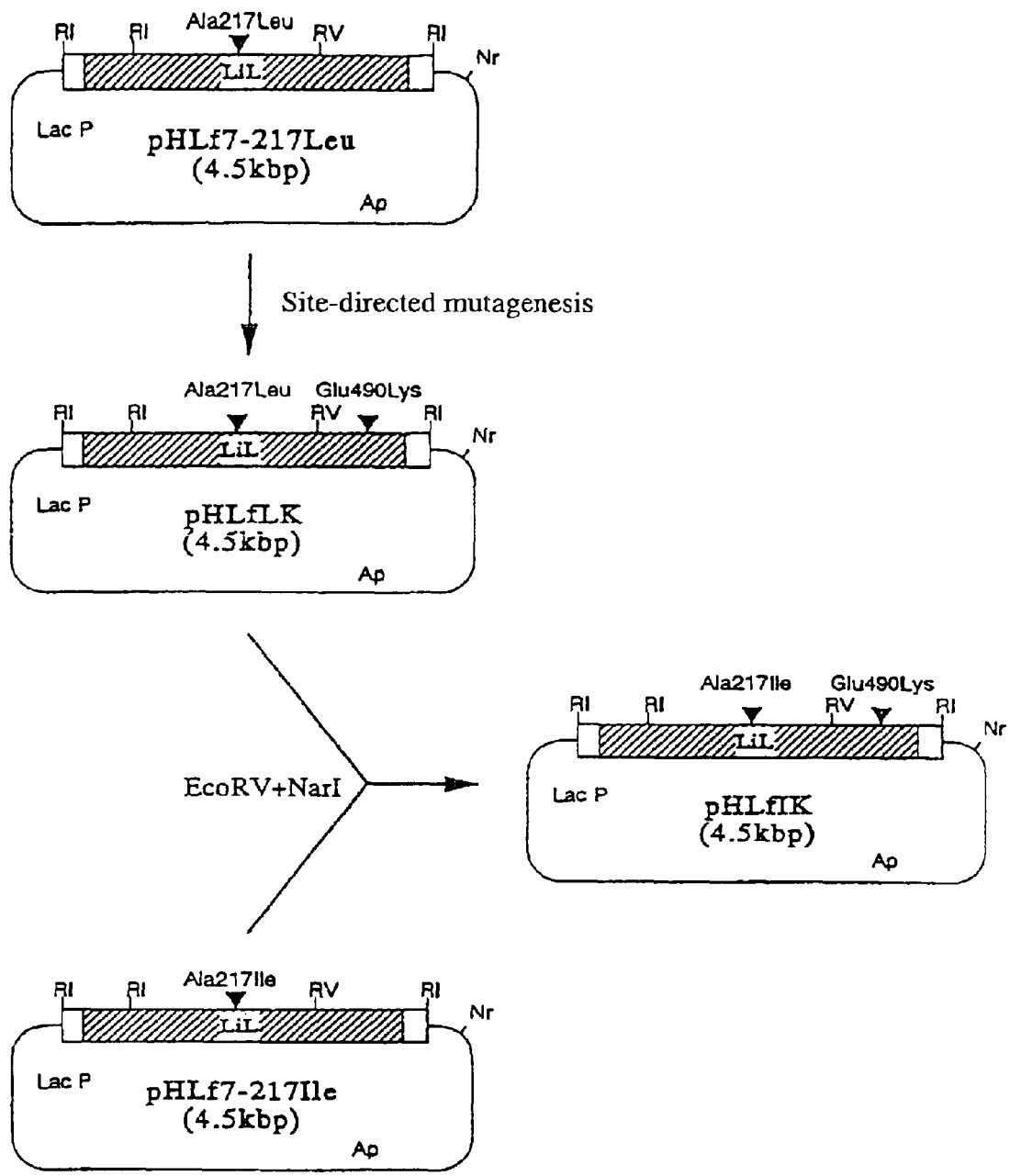
FIG. 1 shows a production processes for a mutant luciferase HIK.

The present invention will now be described in detail.

Luciferase having resistance to surfactant, described below.

The term "having resistance to a surfactant" corresponds to any one of the following features.

(1) When compared to known luciferase, the luciferase of the present invention leads to an increased initial amount of light emitted in the presence of a surfactant. Here the term "compare" means, for example, where the luciferase of the present invention is produced by introducing mutation into an amino acid sequence of known luciferase, to compare light emission from luciferase before and after the introduction of a mutation.

(2) When compared to known luciferase, the luciferase of the present invention shows a gentle decrease in its activity in the presence of a surfactant.

(3) The luciferase of the present invention has the remaining activity of more than 85% in the present of 0.4% surfactant.

Hereinafter "luciferase having resistance to a surfactant" is referred to as "surfactant-resistant luciferase."

The term "activity" means the catalytic activity of bioluminescent reaction. Further any surfactant can be used in the present invention so far as it can be used in the measurement system for intracellular ATP. These surfactants include an anionic surfactant, cationic surfactant, non-ionic surfactant. A specific reagent is benzalkonium chloride or benzetonium chloride containing quaternary ammonium salt as a major component.

The luciferase of the present invention can be prepared from luminescence organs of luminescent organisms. The luminescent organisms include luminescent insects and luminescent bacteria. The luminescent insects include those belonging to the order *Coleoptera*, such as those belonging to the family firefly and the family *Pyrophorus*.

Specific examples include GENJI firefly, HEIKE firefly, North American firefly, Russian firefly, *Pynophorus plagiophthalamus, Arachnocapa luminosa*, and Rail worm. Further the luciferase of the present invention is obtained by cloning a luciferase gene from the luminescent organism and allowing the gene to express using an appropriate vector-host system.

Moreover, the luciferase of the present invention can be obtained by introducing mutation such as additions, deletions, and substitutions into an amino acid sequence of well-known luciferase. Well-known genetic engineering techniques can be used to introduce mutation into an amino acid sequence. In this case firstly, a mutation such as an addition, deletion, or substitution is introduced into a nucleotide sequence of a luciferase gene derived from the above-mentioned luminescent organism or a well-known luciferase gene by genetic engineering techniques so as to generate a mutant luciferase gene. Subsequently, the mutant gene is incorporated into an appropriate host-vector system, thereby generating a recombinant microorganism. Then the recombinant microorganisms producing the luciferase of the present invention are selected by screening. The selected recombinant microorganisms are cultured in a medium. Finally the luciferase can be collected from the culture product.

Hereinafter surfactant-resistant luciferase obtained by introduction of a mutation into an amino acid sequence is referred to as "mutant luciferase."

The mutant luciferase is for example, luciferase wherein an amino acid corresponding to an amino acid at the 490-position of the GENJI firefly luciferase or the HEIKE firefly luciferase, is substituted by an amino acid other than glutamic acid in an amino acid sequence of a wild-type firefly luciferase. The amino acid other than glutamic acid is a basic amino acid. Specific examples include lysine, arginine, and histidine. The term "an amino acid corresponding to the amino acid at the 490-position of the GENJI or the HEIKE firefly luciferase" means an amino acid corresponding to the amino acid at the 490-position of the GENJI or HEIKE firefly luciferase when the determined amino acid sequence of luciferase is compared to an amino acid sequence of the GENJI or HEIKE firefly luciferase.

Moreover, in the GENJI or HEIKE firefly luciferase, the amino acid at the 490-position is glutamic acid. Further, in North American firefly luciferase, "an amino acid corresponding to the amino acid at the 490-position of the GENJI or the HEIKE firefly luciferase" corresponds to the glutamic acid at the 487-position.

More specifically, the mutant luciferase is a polypeptide comprising an amino acid sequence shown in SEQ ID NO:1 or 2, or said amino acid sequence wherein one or more amino acids are added, deleted or substituted.

Method for Producing Mutant Luciferase by Genetic Engineering Techniques

A method for generating mutant luciferase by genetic engineering techniques will now be described as follows.

The mutant luciferase is produced by introducing mutation such as additions, deletions, and substitutions into a nucleotide sequence of known luciferase and allowing an appropriate vector-host system to express the gene.

The known luciferase genes includes, but are not limited to, a firefly luciferase gene, more specifically a wild-type HEIKE firefly luciferase gene (Japanese Patent Application Laid-Open No. 2-171189) and a thermostable HEIKE firefly luciferase gene (Japanese Patent Application Laid-Open No. 5-244942).

i) A method for introducing mutation into a luciferase gene is, for example a method wherein the gene and a mutagen are allowed to contact with each other. Specific examples of the mutagen include hydroxylamine, nitrous acid, sulfurous acid, and 5-bromouracil. Further, ultra violet irradiation, cassette mutagenesis, and site-directed mutagenesis using PCR can also be used. Furthermore, a mutant lucefirase gene having a mutation at a desired position can be generated by annealing chemically synthesized DNA.

ii) Next, the mutant luciferase gene is inserted into a vector DNA having such as a promoter sequence, a marker gene, and a replication origin, etc, thereby producing a recombinant plasmid. Any vector DNA can be used so far as it can be replicated in a host cell. Examples of the vector DNA include plasmid DNA and bacteriophage DNA. When the host cell is *Escherichia coli*, examples of the vector DNA include plasmid pUC119 (Takara Shuzo Co., Ltd.), pBluescript SK+(Stratagene), pMAL-C2 (NEW England Labs), pGEX-5X-1 (Phaimacia), pXal (Boehringer), and pMA56 (G. Ammerer, Meth. Enzymol., 101, 192, 1983).

iii) Subsequently, an appropriate host cell is transformed or transduced with the above recombinant plasmid, and screening is performed for recombinant microorganisms having the ability to produce the mutant luciferase.

Any host cells including eucaryotic and prokaryotic cells can be used. The eucaryotic cells include animal, plant, insect, yeast cells. The prokaryotic cells include *Escherichia coli, Bacillus subtilis,* and *Acrinomyces.* The animal cells include CHO, COS, HeLa cells and cells of myeloma cell lines. The prokaryotic cells include microorganisms belong to the genus *Escherichia,* such as *Escherichia coli* JM101 (ATCC 33876), JM109 (produced by Takara Shuzo Co., Ltd.), XL I-Blue (produced by Stratagene), and HB101 (ATCC33694).

Transformation in the present invention can be performed by for example, D. M. Morrison's method (Meth. Enzymol., 68, 326–331, 1979); Transduction can be conducted by for example, B. Hohn's method (Meth. Enzymol., 68, 299–309, 1979).

Methods for purification of recombinant DNA from recombinant microorganisms include P. Guerry's method (J. Bacteriology, 116, 1064–1066, 1973), and D. B. Clewell's method (J. Bacteriology, 110, 667676, 1972).

The nucleotide sequence of a gene inserted into the recombinant DNA can be determined by, for example Maxam-Gilbert method (Proc. Natl. Acad. Sci. USA, 74, 560–564, 1977), and Dideoxy method (Proc. Natl. Acad. Sci. USA, 74, 5463–5467, 1977).

iv) The mutant luciferase of the present invention can be produced by culturing the recombinant microorganisms obtained in the manner described above in media.

When the host cell is *Escherichia coli,* recombinant *E. coli* may be cultured by solid culture methods, preferably liquid culture methods.

A culture medium of the present invention contains one or more nitrogen sources, such as yeast extract, tryptone, peptone, meat extract, corn steep liquor or exudate of soy bean or wheat bran, to which one or more of inorganic salts, such as sodium chloride, potassium phosphate, dipotassium phosphate, magnesium sulfate, magnesium chloride, ferric chloride, ferric sulfate or manganese sulfate are added. If necessary sugar and vitamins are added to this medium. Further the initial pH of the medium is preferably adjusted within pH 7 to 9. Moreover the culture is performed at a temperature within 30° C. to 42° C., preferably at around 37° C. for 3 to 24 hours, preferably for 5 to 8 hours.

Preferable culture methods include aeration-agitation submerged culture, shaking culture, and static culture.

To recover mutant luciferase from the culture product after the completion of culturing recombinant *E. coli,* standard means for collecting enzymes can be employed. That is, the culture product is centrifuged to obtain cells. Then the cells are disrupted by treatment with lytic enzymes, such as lysozyme, ultrasonication, or milling. Fused protein is discharged out of the cell. Subsequently insoluble substances are removed by filtration or centrifugation, so that a crude enzyme solution containing mutant luciferase can be obtained.

In the present invention the above crude enzyme solution can be used as authetic protein matter, or alternatively it can further be purified to higher purity by standard protein purification techniques. These techniques including sulfate salting out, organic solvent precipitation, ion exchange chromatography, hydrophobic chromatography, gel filtration chromatography, adsorption chromatography, affinity chromatography, and electrophoresis can be used solely or in combination.

The use of surfactant-resistant luciferase of the present invention allows the addition of a surfactant at a high concentration in the extraction process for intracellular ATP. Detection of Intracellular ATP of the Present Invention Detection of intracellular ATP of the present invention will be described as follows.

i) First, ATP extraction reagent containing surfactant as an effective component is added to a sample containing cells so as to extract intracellular ATP out of the cells. The term "cells" refers to the cells derived from animal, plant, microorganism (e.g., yeasts, mold, fungi, bacteria, actinomyces, unicellular algae, viruses, and protozoa).

Any sample can be used so far as it contains the above cells. These samples include, but are not limited to, foods and drinks, pharmaceuticals, cosmetics, seawater, river water, industrial water, sewage, soil, urine, feces, blood, sputum, pus, and culture product of the above cells. A sample solution can also be prepared by suspending these samples in an appropriate solvent, such as distilled water, physiological saline, phosphoric acid buffer, Tris buffer, or sodium acetate buffer. When a fluid specimen contains solids, the fluid specimen is suspended in an appropriate solvent or homogenized using a mixer so that it can be handled in the same manner as that in liquid form.

A sample of a filter membrane can also be prepared by filtering the above sample in liquid form through a hydrophilic or hydrophobic filter membrane. The hydrophilic or hydrophobic filter membrane by which cells are captured can be used as a sample. In such a case, a film- or sheet-type hydrophilic filter membrane made of hydrophilic polytetrafluoroethylene, hydrophilic polyvinylidenefluoride, hydrophilic polyamide, acetylcellulose, and nitrocellulose, etc., can be used. Hydrophobic filter membranes made of PVDF (polyvinylidenefluoride), PTFE (polytorafluoroethylene), and PE (polyethylene) etc., can be used.

Surfactants include anionic surfactants, cationic surfactants, ampholytic surfactants, and non-ionic surfactants.

Anionic sulfactants include sodium dodecyl sulfate (SDS), lauryl potassium sulfate, sodium monolauroyl phosphate, and sodium alkylbenzenesulfonic acid. Cationic surfactants include benzalkonium chloride (BAC), benzetonium chloride (BZC), cetylpyridinium chloride, cethyltrimethylammonium bromide, and myristyldimethylbenzylammonium chloride ampholytic surfactants include Twittergent Detergent 3-08, 3–10, 3-12, 3–14, 3-16, and Tego. Finally non-ionic suifactants include Tween 20, 60, and 80, Span 60 and 80, Triton X-45 and x-100, polyoxyethylene ether, and polyoxyethylene lauryl ether.

Any concentration of a surfactant can be employed so far as it allows full expression of the ability to extract ATP. Preferable concentration of a surfactant is 0.05% or more of the mixture of a sample and ATP extraction reagent.

A sample and ATP extraction reagent are contacted with from each other at room temperature or with heating.

ii) After ATP extraction, bioluminescent reagent is added to the sample containing surfactant-resistant luciferase so as to cause emission. Then the light emission is measured.

When surfactant-resistant luciferase is derived from a firefly, the bioluminescent reagents are those containing e.g., the following components (a) to (c).

(a) surfactant-resistant luciferase
(b) luciferin
(c) magnesium ions or other metal ions Further in addition to the above components, substances involving pH preparation or improved shelf life may be added. Such substances include EDTA 2Na, dithiothreitol, ammonium sulfate, sucrose, 2-mercaptoethanol, HEPES, Tricine, and Tris.

iii) The amount of light emitted by the addition of a bioluminescent reagent can be measured by a luminometer such as a lumitester K-100 produced by kikkoman Corporation, a luminescence reader BLR-201 produced by Aloka Co., Ltd. (an improved type, or a Luriat LB9501 produced by Berthold. When a filter membrane by which cells are captured is used as a sample, the cells can be counted using a bioluminescent image analysis system device to photograph spots on the filter membrane. Such a device is ARGUS-50/CL (with taper fiber: produced by Hamamatsu Photonics K.K.).

The present invention will now be described in detail by the use of examples. However the technical field of the present invention is not limited by these examples.

EXAMPLE 1

Surfactant resistance of natural type luciferase derived from various fire fly species.

Method of Preparing Wild Type Luciferase Derived from Various Firefly Species

Luciferase derived from GENJI and HEIKE fireflies was prepared according to the following methods. 1 mM ethylene diamine-4-acetate-2-sodium and 2 mM phenylmethylsulfonylfluoride were added to 25 mM Tris (hydroxy) aminomethane-hydrochloric acid buffer. Further ammonium sulfate was added to this solution so as to achieve 10% saturation. Tail portions of the various firefly species were added to this mixture at pH 7.8, and then disrupted using Hiskotoron (produced by Nichionrikakikaiseisakusho). The resulting solution was centrifuged at 12,000 r.p.m. for 20 minutes to obtain supernatants as starting materials for purification. The purification was conducted by the process comprising salting out of ammonium sulfate, Ultrogel Ac A34 (produced by LKB) column, and hydroxy-apatite HPLC (produced by TOSHOH, TSK gel HA-1000) column. Finally an electrophoretically homogenous sample was obtained. In addition the luciferase derived from North American firefly is a commercial product (Sigma, L-9506).

Method of Determining Luciferase Activity

A luciferase sample was properly diluted using enzyme-diluted solution (1 nM EDTA, 1 mM 2-mercaptoethanol, 1% BSA, 50 mM HEPES, (pH7.5)). To 100 μl of this solution, 100 μl of substrate solution (1.4 mM luciferin, 40 mM ATP, 300 mM MgSO$_4$. 7H$_2$O, 50 mM HEPES, (pH 7.5)) was added.

The light emission was measured using BLE-201 Luminescence reader (produced by Aloka Co., Ltd.) under the following conditions.

Measuring range: ×100
Numerical value displayed: ×1000
Measuring temperature: 30° C.
Measuring time: 20 seconds 1 MLU (mega light unit)/ml is a value for activity when the measured value under these conditions was 1 Kcount.

Method of Determining Surfactant-Resistance

Enzyme samples were obtained by preparing luciferase samples derived from various firefly species using enzyme-diluted solution (1 mM EDTA, 1 mM 2-mercaptoethanol, 5% glycerol, 50 mM HEPES, (pH7.5)) to achieve 0.5 MLU/ml concentration.

50 μl of 0.4% benzalkonium chloride (25 mM Tricine at pH 7.75) and then 50 μl of the enzyme sample were added to 100 μl of substrate solution (4 mM ATP, 0.4 mM luciferin, 10 mM magnesium sulfate, 50 mM HEPES (pH 7.5)). After the solution was stirred for 5 seconds, the light emission was measured every second using Berthold Lumat LB-9501 for 1 minute.

Figure 2:
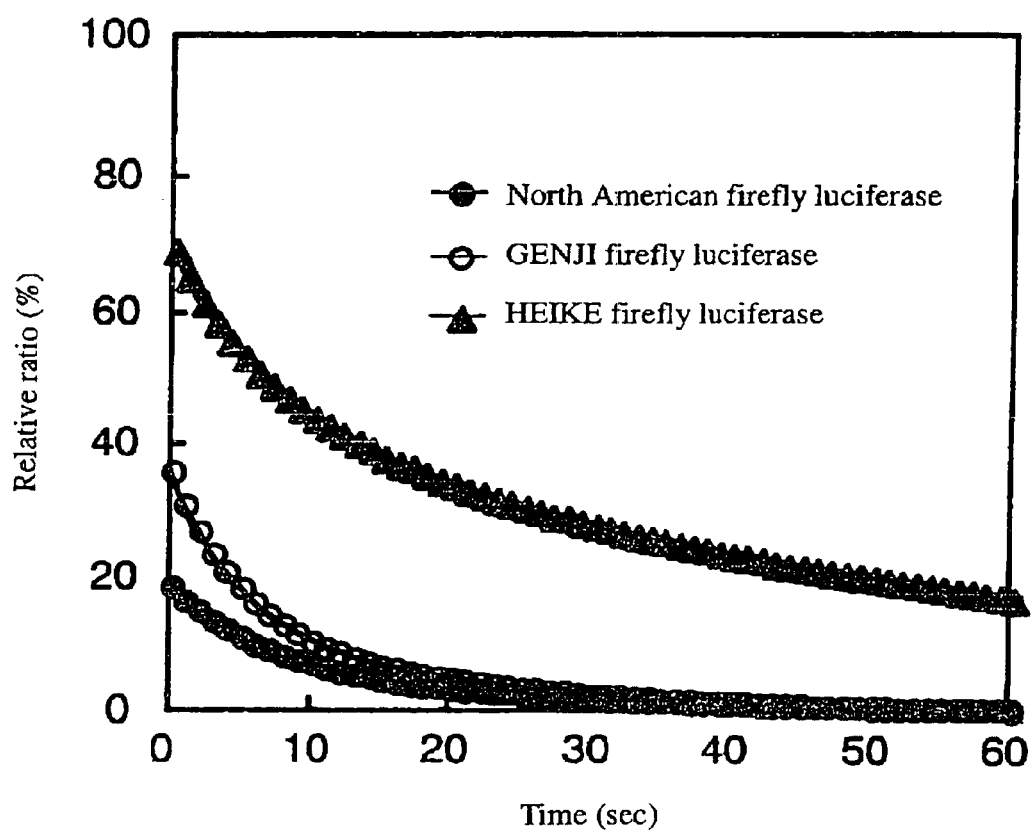
FIG. 2 shows change with time of light emission from natural type luciferase.

FIG. 2 shows the results. Along the vertical axis in this figure, the relative ratio of the light emission was plotted with the initial amount of light emitted considered to be 100% upon use of 25 mM Tricine (pH 7.75) instead of 0.4% benzalkonium chloride.

As shown in these results, North American firefly luciferase was low in the initial light emission and the light emission decayed rapidly. This was caused by the low surfactant-resistance of the North American firefly luciferase. This can lead to low sensitivity and accuracy in measuring such values. On the other hand, GENJI firefly luciferase showed an initial light emission higher than that of North American firefly luciferase. That is, GENJI firefly luciferase was shown to have a surfactant resistance superior to that of North American firefly luciferase. Furthermore, HEIKE firefly luciferase showed an initial light emission higher than that of GENJI firefly luciferase and the emission decayed slowly. Therefore, HEIKE firefly luciferase has good surfactant resistance, superior to that of GENJI firefly luciferase. These results suggest that the degree of surfactant resistance of luciferase varies according to the firefly species.

EXAMPLE 2

Preparation of Mutant Luciferase HLK and HIK

Two types of mutant luciferase (named "HLK" and "HIK") were prepared according to the following methods.

Production of Gene Encoding Mutant Luciferase HIK

A mutant luciferase gene was produced by site-directed mutagenesis using PCR. A plasmid pHLf7-217Leu described in Japanese Patent Application Laid-Open No. 5-244942 was used as a template for PCR reaction. The pHLf7-217Leu was a recombinant plasmid prepared by inserting a thermostable HEIKE firefly luciferase gene, in which an amino acid corresponding to Ala at the 217-position was substituted for a Leu-encoding gene, into a plasmid pUC119. In addition, E. coli JMO11, to which the recombinant plasmid pHLf7-217Leu had been introduced, has been named E. coli JM101 (pHLf7-217Leu) and was deposited on Apr. 22, 1992 as FERM BP-3840 with the National Institute of Bioscience and Human-Technology, Agency of Industrial Science and Technology (1–3, Higashi 1-chome, Tsukuba-shi, Ibaraki-ken, Japan).

The primer for PCR reaction was an oligonuceltide having a nucleotide sequence shown in SEQ ID No: 1 or 2. The DNA polymerase was a KOD dash polymerase (produced by TOYOBO). A PCR reaction cycle (94° C. for 30 seconds, 50° C. for 2 seconds, and 74° C. for 3 minutes) was repeated for 30 times according to the examples attached to KOD dash polymerase. The PCR product was ligated into a circular recombinant plasmid pHLfLK using standard techniques.

Sequencing of a mutant luciferase gene contained in the pHLfLK was performed.

Reaction was conducted using a Diprimer Taq Sequencing Kit (produced by Applied Biosystems). Then the eletrophoretic analysis was performed using ABI 373A DNA sequencer (produced by Applied Biosystems). The entire nucleotide sequence of the obtained mutant luciferase gene is shown in SEQ ID NO: 3, and the amino acid sequence of a polypeptide encoded by this gene is shown in SEQ ID NO: 4. In the mutant luciferase gene, the genetic portion corresponding to alanine at the 217-position of wild-type HEIKE firefly luciferase was substituted by a gene encoding leucine, the genetic portion corresponding to glutamic acid at the 490-position of the same was substituted by a gene encoding lysine. The pHLfLK-introduced E. coli JM109 strain was named E. coli JM109 (pHLfLK) (see FIG. 1). E. coli JM109 (pHLftK) was deposited as FERM BP-6147 on Oct. 16, 1997) with the National Institute of Bioscience and Human-Technology, Agency of Industrial Science and Technology, Japan.

The polypeptide shown in SEQ ID NO:4 was named the mutant luciferase HLK.

Preparation of Gene Encoding Mutant Luciferase HIK

A mutant luciferase gene was prepared using the plasmid pHLf7-217Ile described in Japanese Patent Application Laid-Open No. 5-244942. The plasmid pHLf7-217Ile was a recombinant plasmid prepared by inserting a thermostable HEIKE firefly luciferase gene, in which an amino acid corresponding to Ala at the 217-position was substituted for a Ile-encoding gene, into a plasmid pUC119. The transformant strain obtained using this plasmid was deposited on Apr. 22, 1992 as FERM BP-3841 with the National Institute of Bioscience and Human-Technology, Agency of Industrial Science and Technology, Japan.

About a 560 bp fragment obtained by cutting the pHLftK with EcoRV and NarI was obtained by agarose gel electrophoresis. Then the fragment was inserted into the pHLf7-217Ile treated with the same restriction enzymes.

The resulting recombinant plasmid has been named pHLfIK and the plasmid-introduced E. coli JM109 strain has been named E. coli JM109 (pHLfIK).

E. coli JM109 (pHLfIK) was deposited on Oct. 16, 1997 as FERM BP-6146 with the National Institute of Bioscience and Human-Technology, Agency of Industrial Science and Technology, Japan.

The entire nucleotide sequence of the mutant luciferase gene contained in the pHLfIK is shown in SEQ ID NO: 5, and the amino acid sequence of a polypeptide encoded by this gene is shown in SEQ ID NO: 6. In the mutant luciferase gene, the genetic portion corresponding to alanine at the 217-position of wild-type HEIKE firefly luciferase was substituted by a gene encoding isoleucine, the genetic portion corresponding to glutamtic acid at the 490-position of the same was substituted by a gene encoding lysine (see FIG. 1).

A polypeptide shown in SEQ ID NO:6 was named the mutant HIK firefly.

EXAMPLE 3

Preparation of Mutant Luciferase HLK and HIK

E. coli JM109 (pHLffK) and E. coli JM109 (pHLfIK) were inoculated on LB media (1% Bacto-trypton (W/V), 0.5% yeast extract (WN), 0.5% NaCl (WNT), ampicillin (50 µg/ml), 1.4% agar (W/V)), each containing ampicillin, and cultured at 37° C. for 18 hours. The resulting culture fluid was centrifuged at 8000 r.p.m. for 10 minutes. The precipitated cells were suspended in 0.1M potassium phosphate buffer at pH 7.8 (0.1M ammonium sulfate, 1 mM EDTA) were disrupted by ultrasonication.

Next, crude enzyme solution was obtained by centrifugation at 12000 r.p.m. for 10 minutes. The obtained enzyme solution was purified using the above purification techniques such that it becomes an electrophoretically homogenous sample.

EXAMPLE 4

Surfactant Resistance of Mutant Luciferase HLK and HIK

Changes in Emission with Time

Figure 3:
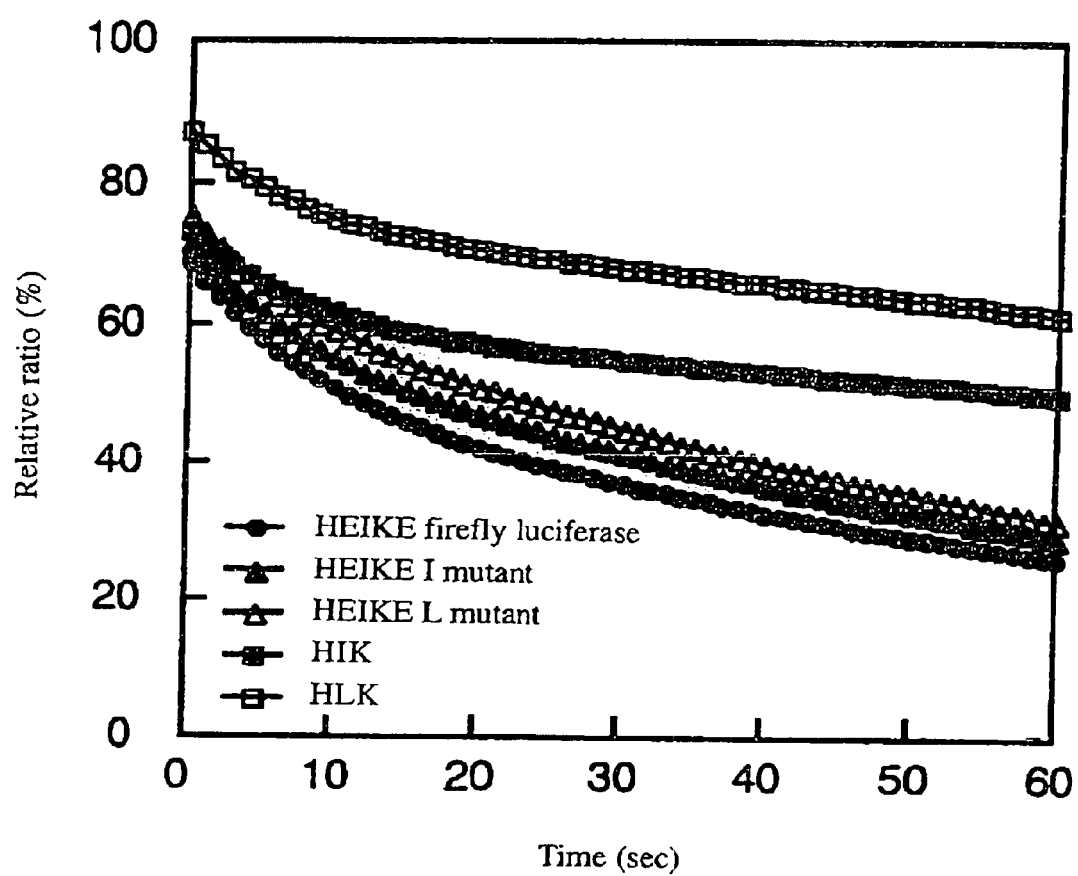
FIG. 3 shows a comparative resistance against benzalkonium chloride of mutant luciferase.
Figure 4:
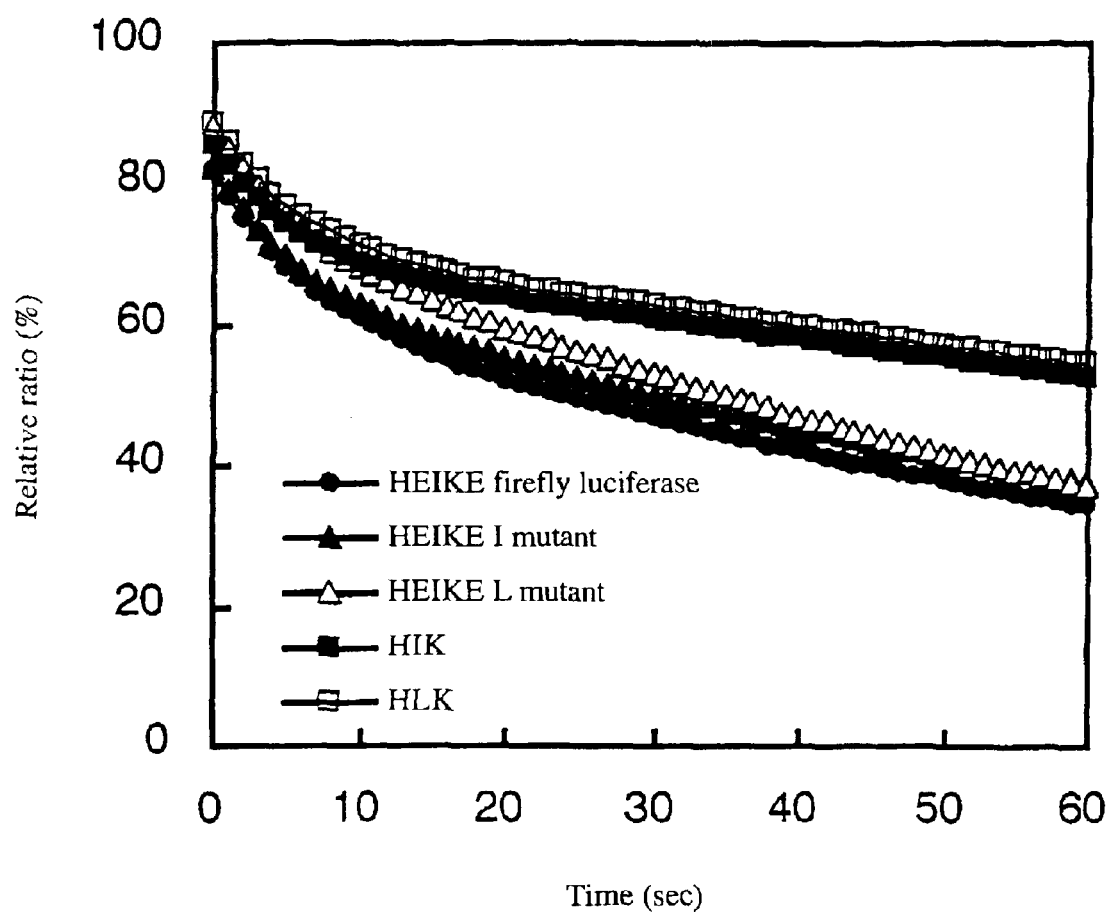
FIG. 4 shows a comparative resistance against benzetonium chloride of mutant luciferase.

To compare surfactant resistance of mutant luciferase with that of known luciferase, changes in emission with time were measured according to the aforementioned methods of measuring surfactant resistance. FIG. 3 shows the results obtained by the use of 0.4% benzalkonium chloride (25 mM Tricine (pH 7.75)). FIG. 4 shows the results obtained by the use of 0.8% benzethonium chloride (25 mM Tricine (pH 7.75)).

"HEIKE I mutant" in this figure is thermostable HEIKE firefly luciferase (described in Japanese Patent Application Laid-Open No. 5-244942) wherein Ala at the 217-position of wild-type HEIKE firefly luciferase is substituted for Ile. "HEIKE L mutant" is thermostable HEIKE firefly luciferase (Japanese Patent Application Laid-Open No. 5-244942) wherein Ala at the 217 position of wild-type HEIKE luciferase is substituted by Leu. "HIK" is a mutant wherein Glu at the 490-position of HEIKE I mutant is substituted by Lys, that is, the mutant luciferase HIK prepared in Example 3. "HLK" is a mutant wherein Glu at the 490-position of HEIKE L mutant is substituted by Lys, that is, the mutant luciferase HLK prepared in Example 3.

As can be seen in FIG. 3 which shows the results for benzalkonium chloride, the emission of HIK decayed more slowly than that of the HEIKE I mutant. Comparison of HLK and HEIKE L mutant reveals that HLK had initial light emission improved by about 20%, and slower decay in the light emission.

Therefore, the substitution of an amino acid at the 490-position resulted in improved surfactant-resistance of a luciferase.

As shown in FIG. 4 which shows the results obtained by the use of benzethonium chloride, HIK showed decay in emission more slowly than that of HEIKE I mutant. Further HLK showed slower decay in light emission than that of HEIKE L mutant. Therefore, the substitution of an amino acid at the 490-position resulted in improved surfactant resistance.

Comparison of Emission Rate

The influence of the enzyme solution, substrate solution and benzalkonium chloride used when measuring change with time, on the measurement values taken under actual emission measurement conditions, was examined. Table 1 shows the light emission measured using Berthold Lumat LB-9501 under measuring conditions (5 seconds of waiting time, 3 seconds of measuring time).

In addition, the emission rate (remaining activity) was calculated by dividing the light emission measured in the presence of 0.4% benzalkonium chloride by a control value.

Here the control value was the light emission upon use of 25 mM Tricine at pH 7.75 instead of 0.4% benzalkonium chloride.

TABLE 1

| | Light emission (RLU) | | |
|---|---|---|---|
| Luciferase type | Without extraction reagent | With extraction reagent | Emission rate (%) |
| North American firefly | 452563 | 97790 | 21.6 |
| GENJI firefly | 409406 | 167805 | 41.0 |
| HEIKE firefly | 425792 | 324724 | 76.3 |
| HEIKE I mutant | 422269 | 341039 | 80.8 |
| HEIKE L mutant | 423728 | 343634 | 81.1 |
| HIK | 386429 | 345159 | 89.3 |
| HLK | 390289 | 396764 | 101.7 |

North American firefly luciferase showed an emission rate as low as 21.6%, suggesting a large decrease in sensitivity. On the other hand, the emission rates for GENJI and HEIKE firefly luciferase were 41.0% and 76.3%, respectively, suggesting that the sensitivity of these firefly luciferases were less affected than that of North American firefly luciferase.

The emission rate for mutant luciferase HIK and HLK were 89.3% and 101.7%, respectively. These rates were far greater than those of wild-type HEIKE firefly luciferase and thermostable HEIKE firefly luciferase. Particularly the emission rate of HLK was almost 1 That is, HLK can yield the same light emission regardless of the presence or absence of a surfactant. Therefore, the sensitivity of HLK is totally unaffected by the use of a surfactant, allowing measurement with high accuracy.

Comparison of $IC_{50}$

Benzalkonium chloride and various luciferases were contacted with each other for 10 minutes. Then the benzalkonium chloride concentration (IC50), at which activity is inactivated by 50% was determined. Equal amounts of luciferase solution prepared at this concentration and 0.01 to 0.1% benzalkonium chloride were mixed, and then allowed to stand for 10 minutes at room temperature. Subsequently, 100 µl of substrate solution was added to the mixture. Immediately after addition, the light emission was measured using Berthold Lumat LB-9501. IC50s obtained were as shown in Table 2.

TABLE 2

$IC_{50}$ for various luciferase

| Luciferase type | $IC_{50}$ (%) |
| --- | --- |
| North American firefly | 0.014 |
| GENJI firefly luciferase | 0.016 |
| HEIKE firefly luciferase | 0.026 |
| HEIKE I mutant | 0.028 |
| HEIKE L mutant | 0.028 |
| HIK | 0.032 |
| HLK | 0.035 |

North American firefly luciferase showed the lowest $IC_{50}$ among the three types of wild-type luciferase. That is, North American firefly luciferase was shown to have the lowest resistance to a surfactant. HEIKE firefly luciferase showed the highest $IC_{50}$ among the wild-type luciferase. HLK and HIK showed $IC_{50}$ higher than those of wild-type HEIKE firefly luciferase and thermostable HEIKE firefly luciferase, suggesting that the resistance was improved by the substitution of an amino acid at the 490-position.

Especially HLK showed $IC_{50}$ higher than that of HIK, indicating that HILK possesses the best surfactant-resistance.

EXAMPLE 5

Method for Measuring Intracellular ATP

Next, a method for measuring intracellular ATP using the surfactant-resistant luciferase of the present invention will be described.

A standard technique used herein was TCA extraction method wherein intracellular ATP is extracted using trichloroacetic acid (TCA) and the amount of ATP extracted is measured using luciferin-luciferase luminescence reaction. TCA extraction method is excellent in extraction efficiency. Further in TCA extraction method no inhibition of luminescence reaction is caused by TCA because emission is measured after the sample containing TCA is diluted 1:100. Because of this dilution, however, TCA extraction method is complicated and can cause a decrease in the measuring sensitivity.

1. Materials (1) Surfactant

Benzalkonium chloride (BAC, Japanese Pharmacopoeia) was used. ATP extraction reagent was prepared by dissolving this surfactant at 0.25% concentration into 25 mM Tricine (pH 7.75).

(2) Microorganisms

Four strains, *Escherichia coli* (ATCC 25922), *Staphylococcus aureus* (ATCC 25923), *Pseudomonas aeruginosa* (ATCC 27853) and *Enterococcus faecalis* (ATCC 29212) were used.

(3) Preparation of Samples

In standard techniques, a sample, undiluted solution, was prepared by culturing the prescribed microorganisms on a normal broth medium (produced by Eiken chemical Co., Ltd.) at 35° C. overnight. In the method of the present invention, a sample diluted solution was prepared by diluting an undiluted solution of the culture fluid to 1:100 with sterile water.

(4) Luciferase

Surfactant-resistant luciferase of the present invention were HIK and HLK. Control surfactant-resistant luciferase types were known luciferase (North American firefly luciferase, GENJI firefly luciferase, HEIKE firefly luciferase, HEIKE I mutant, and HEIKE L mutant).

(5) Luminescence Reagent

Luminescence reagent was prepared by adding various luciferase to solution containing 0.15 mM luciferin, 6 mM EDTA, 15 mM magnesium acetate, 0.2 mM dithiothreitol, 0.5% BSA and 25 mM HEPES (pH 7.75).

The amount of luciferase to be added was prepared such that the light emission produced when 100 µl of $2\times10^{-8}$ M ATP standard solution was added to 100 µl of the luminescence reagent would be the same amount of the light emission produced when a luminescence reagent attached to Luciferase LU (Kikkoman Corporation) was used.

2. Method for Measuring Intracellular ATP (1) Method of the Present Invention

ATP extraction reagent 100 µl was added to 100 µl of a sample. The solution was allowed to stand for 20 seconds at room temperature. Then 100 µl of the luminescence reagent was added to this solution. Immediately after addition, the light emission was measured using Lumat LB-9501 produced by Berthold.

(2) Standard Technique

10% trichloro acetate solution 100 µl was added to 100 µl of a sample and the solution was allowed to stand for 1 minute. 25 mM Tricine (pH 7.75) 9.8 ml was added to this extract, and then the extract was well stirred. 25 mM Tricine (pH 7.75) and 100 µl of a luminescence reagent attached to CheckLite LU (produced by Kikkoman Corporation) were added to 100 l of the sample. Immediately after addition, the light emission was measured using Lumat LB-9501 produced by Berthold.

3. Results

Tables 3 and 4 show the results. The relative ratio of the light emissions obtained by the use of the luminescence reagents using various luciferase types is also shown in these tables. Here the light emission obtained by the standard technique (TCA extraction method) was defined as 100%.

TABLE 3

Detection of intracellular ATP

| | E. coli ATCC25922 | | S. aureus ATCC 25923 | |
| --- | --- | --- | --- | --- |
| Measuring method | Measured value (RLU) | Relative ratio (%) | Measured value (RLU) | Relative ratio (%) |
| Standard technique (TCA extraction method) | 132794 | (100.0) | 130220 | (100.0) |

TABLE 3-continued

Detection of intracellular ATP

| Measuring method | E. coli ATCC25922 | | S. aureus ATCC 25923 | |
|---|---|---|---|---|
| | Measured value (RLU) | Relative ratio (%) | Measured value (RLU) | Relative ratio (%) |
| North American firefly | 153 | (0.1) | 163 | (0.1) |
| GENJI firefly luciferase | 463 | (0.3) | 659 | (0.5) |
| HEIKE firefly luciferase | 76082 | (57.3) | 74019 | (56.8) |
| HEIKE I mutant | 47655 | (35.9) | 50031 | (38.4) |
| HEIKE L mutant | 46217 | (34.8) | 51243 | (39.4) |
| HIK | 97073 | (73.1) | 76533 | (58.8) |
| HLK | 87981 | (66.3) | 72182 | (55.4) |

TABLE 4

Detection of intracellular ATP

| Measuring method | P. aeruginosa ATCC 27853 | | E. faecalis ATCC 29212 | |
|---|---|---|---|---|
| | Measured value (RLU) | Relative ratio (%) | Measured value (RLU) | Relative ratio (%) |
| Standard technique (TCA extraction method) | 168141 | (100.0) | 12427 | (100.0) |
| North American firefly | 553 | (0.3) | 113 | (0.1) |
| GENJI firefly luciferase | 1503 | (0.9) | 163 | (1.3) |
| HEIKE firefly luciferase | 117096 | (69.6) | 8132 | (65.4) |
| HEIKE I mutant | 80455 | (47.8) | 4586 | (36.9) |
| HEIKE L mutant | 81069 | (48.2) | 4762 | (38.3) |
| HIK | 131134 | (78.0) | 7914 | (63.7) |
| HLK | 131815 | (78.4) | 7998 | (64.4) |

No emission was observed for the luminescence reagent containing North American firefly luciferase. GENJI firefly luciferase showed weak emission. This is because the luciferase itself was devitalized by the surfactant. Therefore, it was shown that the surfactant at high concentration such as was used in this examination cannot be used as an ATP extraction reagent for the luciferase.

Unlike North American firefly luciferase and GENJI firefly luciferase, HEIKE firefly luciferase showed emission 60 to 70% of that in TCA extraction method. HEIKE firefly luciferase was shown to possess surfactant-resistance higher than those of North American firefly luciferase and GENJI firefly luciferase.

Light emissions from HEIKE L mutant, and HEIKE I mutant which is thermostable HEIKE firefly luciferase were each equivalent to around 40% of that in TCA extraction method, and largely lower than that of wild-type HEIKE firefly luciferase.

Each of the light emission from HIK and RLK, which is surfactant-resistant luciferase of the present invention, respectively was more intense than that from wild-type HEIKE luciferase and thermostable luciferase. Further the light emission in this case was equivalent to 60 to 80% of that in TCA extraction method.

HIK and HLK are mutants wherein Glu at the 490-position of HEIKE I and HEIKE L mutants are substituted for Lys, respectively. That is, the introduction of said mutation into the amino acid at the 490-position improved resistance to a surfactant. The sensitivity of HIK and HLK is less affected by ATP extraction reagent even at such a high concentration employed in this examination, suggesting the use of HIK and HLK enable highly accurate measurement.

INDUSTRIAL APPLICABILITY

The use of a novel surfactant-resistant luciferase according to the present invention for measuring intracellular ATP allows the detection without a decrease in luciferase activity even in the presence of a surfactant at a high concentration.

All publications, patents and patent applications cited herein are incorporated herein by reference in their entirety.
Sequence Listing Free Text
SEQ ID NO:1: A synthetic DNA
SEQ ID NO:2: A synthetic DNA

What is claimed is:

1. A polypeptide comprising:

SEQ ID NO: 8, except that the amino acid residue at position 490 is an amino acid other than glutamic acid, or a fragment of SEQ ID NO: 8 except that the amino acid residue at position number 490 is an amino acid other than glutamic acid, wherein said fragment has luciferase activity and retains more than 85% of its luciferase activity in the presence of 0.1% benzalkonium chloride compared to its luciferase activity as measured in the absence of benzalkonium chloride.

2. The polypeptide of claim 1 which comprises SEQ ID NO: 8, except that the amino acid residue at position number 490 is an amino acid other than glutamic acid.

3. The polypeptide of claim 1 which comprises a fragment of SEQ ID NO: 8, except that the amino acid residue at position number 490 is an amino acid other than glutamic acid.

4. A polypeptide comprising SEQ ID NO: 4 or a fragment of SEQ ID NO: 4, wherein said fragment has luciferase activity and retains more than 85% of its luciferase activity in the presence of 0.1% benzalkonium chloride compared to its luciferase activity as measured in the absence of benzalkonium chloride.

5. A polypeptide comprising SEQ ID NO: 6 or a fragment of SEQ ID NO: 6, wherein said fragment has luciferase activity and retains more than 85% of its luciferase activity in the presence of 0.1% benzalkonium chloride compared to its luciferase activity as measured in the absence of benzalkonium chloride.

6. A nucleic acid encoding a polypeptide comprising:

SEQ ID NO: 8 except that the amino acid residue at position 490 is an amino acid other than glutamic acid, or a fragment of SEQ ID NO: 8 except that the amino acid residue at position number 490 is an amino acid other than glutamic acid, wherein said fragment has luciferase activity and retains more than 85% of its luciferase activity in the presence of 0.1% benzalkonium chloride compared to its luciferase activity as measured in the absence of benzalkonium chloride.

7. The nucleic acid of claim 6 which encodes a polypeptide comprising SEQ ID NO: 8, except that the amino acid residue at position number 490 is an amino acid other than glutamic acid.

8. The nucleic acid of claim 6 which encodes a polypeptide fragment of SEQ ID NO: 8, except that the amino acid residue at position number 490 is an amino acid other than glutamic acid.

9. A nucleic acid that encodes a polypeptide comprising SEQ ID NO: 4 or a fragment of SEQ ID NO: 4, wherein said fragment has luciferase activity and retains more than 85% of its luciferase activity in the presence of 0.1% benzalkonium chloride compared to its luciferase activity as measured in the absence of benzalkonium chloride.

10. The nucleic acid of claim 9 that comprises SEQ ID NO: 3 or a fragment of SEQ ID NO: 3.

11. A nucleic acid that encodes a polypeptide comprising SEQ ID NO: 6 or a fragment of SEQ ID NO: 6, wherein said fragment has luciferase activity and retains more than 85% of its luciferase activity in the presence of 0.1% benzalkonium chloride compared to its luciferase activity as measured in the absence of benzalkonium chloride.

12. The nucleic acid of claim 11 that comprises SEQ ID NO: 5 or a fragment of SEQ ID NO: 5.

13. A vector comprising the nucleic acid of claim 6.

14. A vector comprising the nucleic acid of claim 9.

15. A vector comprising the nucleic acid of claim 11.

16. A host cell comprising the nucleic acid of claim 6.

17. A host cell comprising the nucleic acid of claim 9.

18. A host cell comprising the nucleic acid of claim 11.

19. A method for producing a polypeptide having luciferase activity comprising culturing the host cell of claim 16 in a medium suitable for expression of said nucleic acid.

20. A method for producing a polypeptide having luciferase activity comprising culturing the host cell of claim 17 in a medium suitable for expression of said nucleic acid.

21. A method for producing a polypeptide having luciferase activity comprising culturing the host cell of claim 18 in a medium suitable for expression of said nucleic acid.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
tgttgtactt aagaaaggaa aat                                         23

<210> SEQ ID NO 2
<211> LENGTH: 23
<212> TYPE: DNA
<213> ORGANISM: ARTIFICIAL SEQUENCE
<220> FEATURE:
<223> OTHER INFORMATION: SYNTHETIC DNA

```
<400> SEQUENCE: 2
acagctcccg gaagctcacc agc                                           23

<210> SEQ ID NO 3
<211> LENGTH: 1644
<212> TYPE: DNA
<213> ORGANISM: Luciola lateralis
<220> FEATURE:
<221> NAME/KEY: CDS
<222> LOCATION: (1)..(1644)

<400> SEQUENCE: 3 atg gaa aac atg gag aac gat gaa aat att gtg tat ggt cct gaa cca      48
Met Glu Asn Met Glu Asn Asp Glu Asn Ile Val Tyr Gly Pro Glu Pro
1               5                   10                  15 ttt tac cct att gaa gag gga tct gct gga gca caa ttg cgc aag tat      96
Phe Tyr Pro Ile Glu Glu Gly Ser Ala Gly Ala Gln Leu Arg Lys Tyr
                20                  25                  30 atg gat cga tat gca aaa ctt gga gca att gct ttt act aac gca ctt     144
Met Asp Arg Tyr Ala Lys Leu Gly Ala Ile Ala Phe Thr Asn Ala Leu
            35                  40                  45 acc ggt gtc gat tat acg tac gcc gaa tac tta gaa aaa tca tgc tgt     192
Thr Gly Val Asp Tyr Thr Tyr Ala Glu Tyr Leu Glu Lys Ser Cys Cys
50                  55                  60 cta gga gag gct tta aag aat tat ggt ttg gtt gtt gat gga aga att     240
Leu Gly Glu Ala Leu Lys Asn Tyr Gly Leu Val Val Asp Gly Arg Ile
65                  70                  75                  80 gcg tta tgc agt gaa aac tgt gaa gaa ttc ttt att cct gta tta gcc     288
Ala Leu Cys Ser Glu Asn Cys Glu Glu Phe Phe Ile Pro Val Leu Ala
                85                  90                  95 ggt tta ttt ata ggt gtc ggt gtg gct cca act aat gag att tac act     336
Gly Leu Phe Ile Gly Val Gly Val Ala Pro Thr Asn Glu Ile Tyr Thr
                100                 105                 110 cta cgt gaa ttg gtt cac agt tta ggc atc tct aag cca aca att gta     384
Leu Arg Glu Leu Val His Ser Leu Gly Ile Ser Lys Pro Thr Ile Val
            115                 120                 125 ttt agt tct aaa aaa gga tta gat aaa gtt ata act gta caa aaa acg     432
Phe Ser Ser Lys Lys Gly Leu Asp Lys Val Ile Thr Val Gln Lys Thr
        130                 135                 140 gta act gct att aaa acc att gtt ata ttg gac agc aaa gtg gat tat     480
Val Thr Ala Ile Lys Thr Ile Val Ile Leu Asp Ser Lys Val Asp Tyr
145                 150                 155                 160 aga ggt tat caa tcc atg gac aac ttt att aaa aaa aac act cca caa     528
Arg Gly Tyr Gln Ser Met Asp Asn Phe Ile Lys Lys Asn Thr Pro Gln
                165                 170                 175 ggt ttc aaa gga tca agt ttt aaa act gta gaa gtt aac cgc aaa gaa     576
Gly Phe Lys Gly Ser Ser Phe Lys Thr Val Glu Val Asn Arg Lys Glu
            180                 185                 190 caa gtt gct ctt ata atg aac tct tcg ggt tca acc ggt ttg cca aaa     624
Gln Val Ala Leu Ile Met Asn Ser Ser Gly Ser Thr Gly Leu Pro Lys
        195                 200                 205 ggt gtg caa ctt act cat gaa aat ttg gtc act aga ttt tct cac gct     672
Gly Val Gln Leu Thr His Glu Asn Leu Val Thr Arg Phe Ser His Ala
    210                 215                 220 aga gat cca att tat gga aac caa gtt tca cca ggc acg gct att tta     720
Arg Asp Pro Ile Tyr Gly Asn Gln Val Ser Pro Gly Thr Ala Ile Leu
225                 230                 235                 240 act gta gta cca ttc cat cat ggt ttt ggt atg ttt act act tta ggc     768
Thr Val Val Pro Phe His His Gly Phe Gly Met Phe Thr Thr Leu Gly
                245                 250                 255
```

-continued

| | |
|---|---|
| tat cta act tgt ggt ttt cgt att gtc atg tta acg aaa ttt gac gaa<br>Tyr Leu Thr Cys Gly Phe Arg Ile Val Met Leu Thr Lys Phe Asp Glu<br>260                          265                         270 | 816 |
| gag act ttt tta aaa aca ctg caa gat tac aaa tgt tca agc gtt att<br>Glu Thr Phe Leu Lys Thr Leu Gln Asp Tyr Lys Cys Ser Ser Val Ile<br>     275                        280                        285 | 864 |
| ctt gta ccg act ttg ttt gca att ctt aat aga agt gaa tta ctc gat<br>Leu Val Pro Thr Leu Phe Ala Ile Leu Asn Arg Ser Glu Leu Leu Asp<br>290                         295                       300 | 912 |
| aaa tat gat tta tca aat tta gtt gaa att gca tct ggc gga gca cct<br>Lys Tyr Asp Leu Ser Asn Leu Val Glu Ile Ala Ser Gly Gly Ala Pro<br>305                        310                      315                 320 | 960 |
| tta tct aaa gaa att ggt gaa gct gtt gct aga cgt ttt aat tta ccg<br>Leu Ser Lys Glu Ile Gly Glu Ala Val Ala Arg Arg Phe Asn Leu Pro<br>               325                       330                      335 | 1008 |
| ggt gtt cgt caa ggc tat ggt tta aca gaa aca acc tct gca att att<br>Gly Val Arg Gln Gly Tyr Gly Leu Thr Glu Thr Thr Ser Ala Ile Ile<br>          340                       345                     350 | 1056 |
| atc aca ccg gaa ggc gat gat aaa cca ggt gct tct ggc aaa gtt gtg<br>Ile Thr Pro Glu Gly Asp Asp Lys Pro Gly Ala Ser Gly Lys Val Val<br>355                         360                      365 | 1104 |
| cca tta ttt aaa gca aaa gtt atc gat ctt gat act aaa aaa act ttg<br>Pro Leu Phe Lys Ala Lys Val Ile Asp Leu Asp Thr Lys Lys Thr Leu<br>370                         375                      380 | 1152 |
| ggc ccg aac aga cgt gga gaa gtt tgt gta aag ggt cct atg ctt atg<br>Gly Pro Asn Arg Arg Gly Glu Val Cys Val Lys Gly Pro Met Leu Met<br>385                        390                      395                 400 | 1200 |
| aaa ggt tat gta gat aat cca gaa gca aca aga gaa atc ata gat gaa<br>Lys Gly Tyr Val Asp Asn Pro Glu Ala Thr Arg Glu Ile Ile Asp Glu<br>                   405                       410                      415 | 1248 |
| gaa ggt tgg ttg cac aca gga gat att ggg tat tac gat gaa gaa aaa<br>Glu Gly Trp Leu His Thr Gly Asp Ile Gly Tyr Tyr Asp Glu Glu Lys<br>420                         425                      430 | 1296 |
| cat ttc ttt atc gtg gat cgt ttg aag tct tta atc aaa tac aaa gga<br>His Phe Phe Ile Val Asp Arg Leu Lys Ser Leu Ile Lys Tyr Lys Gly<br>               435                       440                      445 | 1344 |
| tat caa gta cca cct gct gaa tta gaa tct gtt ctt ttg caa cat cca<br>Tyr Gln Val Pro Pro Ala Glu Leu Glu Ser Val Leu Leu Gln His Pro<br>450                         455                      460 | 1392 |
| aat att ttt gat gcc ggc gtt gct ggc gtt cca gat cct ata gct ggt<br>Asn Ile Phe Asp Ala Gly Val Ala Gly Val Pro Asp Pro Ile Ala Gly<br>465                        470                      475                 480 | 1440 |
| gag ctt ccg gga gct gtt gtt gta ctt aag aaa gga aaa tct atg act<br>Glu Leu Pro Gly Ala Val Val Val Leu Lys Lys Gly Lys Ser Met Thr<br>               485                       490                      495 | 1488 |
| gaa aaa gaa gta atg gat tac gtt gct agt caa gtt tca aat gca aaa<br>Glu Lys Glu Val Met Asp Tyr Val Ala Ser Gln Val Ser Asn Ala Lys<br>          500                       505                     510 | 1536 |
| cgt ttg cgt ggt ggt gtc cgt ttt gtg gac gaa gta cct aaa ggt ctc<br>Arg Leu Arg Gly Gly Val Arg Phe Val Asp Glu Val Pro Lys Gly Leu<br>515                         520                      525 | 1584 |
| act ggt aaa att gac ggt aaa gca att aga gaa ata ctg aag aaa cca<br>Thr Gly Lys Ile Asp Gly Lys Ala Ile Arg Glu Ile Leu Lys Lys Pro<br>530                         535                      540 | 1632 |
| gtt gct aag atg<br>Val Ala Lys Met<br>545 | 1644 |

```
<210> SEQ ID NO 4
<211> LENGTH: 548
<212> TYPE: PRT
<213> ORGANISM: Luciola lateralis

<400> SEQUENCE: 4

Met Glu Asn Met Glu Asn Asp Glu Asn Ile Val Tyr Gly Pro Glu Pro
  1               5                  10                  15

Phe Tyr Pro Ile Glu Glu Gly Ser Ala Gly Ala Gln Leu Arg Lys Tyr
                 20                  25                  30

Met Asp Arg Tyr Ala Lys Leu Gly Ala Ile Ala Phe Thr Asn Ala Leu
             35                  40                  45

Thr Gly Val Asp Tyr Thr Tyr Ala Glu Tyr Leu Glu Lys Ser Cys Cys
 50                  55                  60

Leu Gly Glu Ala Leu Lys Asn Tyr Gly Leu Val Val Asp Gly Arg Ile
 65                  70                  75                  80

Ala Leu Cys Ser Glu Asn Cys Glu Glu Phe Phe Ile Pro Val Leu Ala
                 85                  90                  95

Gly Leu Phe Ile Gly Val Gly Val Ala Pro Thr Asn Glu Ile Tyr Thr
                100                 105                 110

Leu Arg Glu Leu Val His Ser Leu Gly Ile Ser Lys Pro Thr Ile Val
            115                 120                 125

Phe Ser Ser Lys Lys Gly Leu Asp Lys Val Ile Thr Val Gln Lys Thr
        130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Leu Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
            260                 265                 270

Glu Thr Phe Leu Lys Thr Leu Gln Asp Tyr Lys Cys Ser Ser Val Ile
        275                 280                 285

Leu Val Pro Thr Leu Phe Ala Ile Leu Asn Arg Ser Glu Leu Leu Asp
    290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Thr Leu
    370                 375                 380
```

```
Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
            405                 410                 415

Glu Gly Trp Leu His Thr Gly Asp Ile Gly Tyr Tyr Asp Glu Lys
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
    450                 455                 460

Asn Ile Phe Asp Ala Gly Val Ala Gly Val Pro Asp Pro Ile Ala Gly
465                 470                 475                 480

Glu Leu Pro Gly Ala Val Val Leu Lys Lys Gly Lys Ser Met Thr
            485                 490                 495

Glu Lys Glu Val Met Asp Tyr Val Ala Ser Gln Val Ser Asn Ala Lys
        500                 505                 510

Arg Leu Arg Gly Gly Val Arg Phe Val Asp Glu Val Pro Lys Gly Leu
    515                 520                 525

Thr Gly Lys Ile Asp Gly Lys Ala Ile Arg Glu Ile Leu Lys Lys Pro
    530                 535                 540

Val Ala Lys Met
545

<210> SEQ ID NO 5
<211> LENGTH: 1644
<212> TYPE: DNA
<213> ORGANISM: Luciola lateralis
<220> FEATURE:
<221> NAME/KEY: CDS
<222> LOCATION: (1)..(1644)

<400> SEQUENCE: 5 atg gaa aac atg gag aac gat gaa aat att gtg tat ggt cct gaa cca      48
Met Glu Asn Met Glu Asn Asp Glu Asn Ile Val Tyr Gly Pro Glu Pro
1               5                   10                  15 ttt tac cct att gaa gag gga tct gct gga gca caa ttg cgc aag tat      96
Phe Tyr Pro Ile Glu Glu Gly Ser Ala Gly Ala Gln Leu Arg Lys Tyr
                20                  25                  30 atg gat cga tat gca aaa ctt gga gca att gct ttt act aac gca ctt     144
Met Asp Arg Tyr Ala Lys Leu Gly Ala Ile Ala Phe Thr Asn Ala Leu
            35                  40                  45 acc ggt gtc gat tat acg tac gcc gaa tac tta gaa aaa tca tgc tgt     192
Thr Gly Val Asp Tyr Thr Tyr Ala Glu Tyr Leu Glu Lys Ser Cys Cys
        50                  55                  60 cta gga gag gct tta aag aat tat ggt ttg gtt gtt gat gga aga att     240
Leu Gly Glu Ala Leu Lys Asn Tyr Gly Leu Val Val Asp Gly Arg Ile
65                  70                  75                  80 gcg tta tgc agt gaa aac tgt gaa gaa ttc ttt att cct gta tta gcc     288
Ala Leu Cys Ser Glu Asn Cys Glu Glu Phe Phe Ile Pro Val Leu Ala
                85                  90                  95 ggt tta ttt ata ggt gtc ggt gtg gct cca act aat gag att tac act     336
Gly Leu Phe Ile Gly Val Gly Val Ala Pro Thr Asn Glu Ile Tyr Thr
                100                 105                 110 cta cgt gaa ttg gtt cac agt tta ggc atc tct aag cca aca att gta     384
Leu Arg Glu Leu Val His Ser Leu Gly Ile Ser Lys Pro Thr Ile Val
            115                 120                 125 ttt agt tct aaa aaa gga tta gat aaa gtt ata act gta caa aaa acg     432
Phe Ser Ser Lys Lys Gly Leu Asp Lys Val Ile Thr Val Gln Lys Thr
        130                 135                 140
```

-continued

| | | |
|---|---|---|
| gta act gct att aaa acc att gtt ata ttg gac agc aaa gtg gat tat<br>Val Thr Ala Ile Lys Thr Ile Val Ile Leu Asp Ser Lys Val Asp Tyr<br>145                 150                  155             160 | 480 |
| aga ggt tat caa tcc atg gac aac ttt att aaa aaa aac act cca caa<br>Arg Gly Tyr Gln Ser Met Asp Asn Phe Ile Lys Lys Asn Thr Pro Gln<br>                165                 170                175 | 528 |
| ggt ttc aaa gga tca agt ttt aaa act gta gaa gtt aac cgc aaa gaa<br>Gly Phe Lys Gly Ser Ser Phe Lys Thr Val Glu Val Asn Arg Lys Glu<br>            180                   185               190 | 576 |
| caa gtt gct ctt ata atg aac tct tcg ggt tca acc ggt ttg cca aaa<br>Gln Val Ala Leu Ile Met Asn Ser Ser Gly Ser Thr Gly Leu Pro Lys<br>195                200                  205 | 624 |
| ggt gtg caa ctt act cat gaa aat atc gtc act aga ttt tct cac gct<br>Gly Val Gln Leu Thr His Glu Asn Ile Val Thr Arg Phe Ser His Ala<br>210                215                  220 | 672 |
| aga gat cca att tat gga aac caa gtt tca cca ggc acg gct att tta<br>Arg Asp Pro Ile Tyr Gly Asn Gln Val Ser Pro Gly Thr Ala Ile Leu<br>225                230                  235             240 | 720 |
| act gta gta cca ttc cat cat ggt ttt ggt atg ttt act act tta ggc<br>Thr Val Val Pro Phe His His Gly Phe Gly Met Phe Thr Thr Leu Gly<br>                  245                250             255 | 768 |
| tat cta act tgt ggt ttt cgt att gtc atg tta acg aaa ttt gac gaa<br>Tyr Leu Thr Cys Gly Phe Arg Ile Val Met Leu Thr Lys Phe Asp Glu<br>            260                  265             270 | 816 |
| gag act ttt tta aaa aca ctg caa gat tac aaa tgt tca agc gtt att<br>Glu Thr Phe Leu Lys Thr Leu Gln Asp Tyr Lys Cys Ser Ser Val Ile<br>275              280                285 | 864 |
| ctt gta ccg act ttg ttt gca att ctt aat aga agt gaa tta ctc gat<br>Leu Val Pro Thr Leu Phe Ala Ile Leu Asn Arg Ser Glu Leu Leu Asp<br>290                295                300 | 912 |
| aaa tat gat tta tca aat tta gtt gaa att gca tct ggc gga gca cct<br>Lys Tyr Asp Leu Ser Asn Leu Val Glu Ile Ala Ser Gly Gly Ala Pro<br>305              310              315             320 | 960 |
| tta tct aaa gaa att ggt gaa gct gtt gct aga cgt ttt aat tta ccg<br>Leu Ser Lys Glu Ile Gly Glu Ala Val Ala Arg Arg Phe Asn Leu Pro<br>                  325                330             335 | 1008 |
| ggt gtt cgt caa ggc tat ggt tta aca gaa aca acc tct gca att att<br>Gly Val Arg Gln Gly Tyr Gly Leu Thr Glu Thr Thr Ser Ala Ile Ile<br>            340                  345             350 | 1056 |
| atc aca ccg gaa ggc gat gat aaa cca ggt gct tct ggc aaa gtt gtg<br>Ile Thr Pro Glu Gly Asp Asp Lys Pro Gly Ala Ser Gly Lys Val Val<br>355                360                  365 | 1104 |
| cca tta ttt aaa gca aaa gtt atc gat ctt gat act aaa aaa act ttg<br>Pro Leu Phe Lys Ala Lys Val Ile Asp Leu Asp Thr Lys Lys Thr Leu<br>370                375                380 | 1152 |
| ggc ccg aac aga cgt gga gaa gtt tgt gta aag ggt cct atg ctt atg<br>Gly Pro Asn Arg Arg Gly Glu Val Cys Val Lys Gly Pro Met Leu Met<br>385                390                395             400 | 1200 |
| aaa ggt tat gta gat aat cca gaa gca aca aga gaa atc ata gat gaa<br>Lys Gly Tyr Val Asp Asn Pro Glu Ala Thr Arg Glu Ile Ile Asp Glu<br>                  405                410             415 | 1248 |
| gaa ggt tgg ttg cac aca gga gat att ggg tat tac gat gaa gaa aaa<br>Glu Gly Trp Leu His Thr Gly Asp Ile Gly Tyr Tyr Asp Glu Glu Lys<br>            420                  425             430 | 1296 |
| cat ttc ttt atc gtg gat cgt ttg aag tct tta atc aaa tac aaa gga<br>His Phe Phe Ile Val Asp Arg Leu Lys Ser Leu Ile Lys Tyr Lys Gly<br>435                440                445 | 1344 |
| tat caa gta cca cct gct gaa tta gaa tct gtt ctt ttg caa cat cca<br>Tyr Gln Val Pro Pro Ala Glu Leu Glu Ser Val Leu Leu Gln His Pro<br>450                455                460 | 1392 |

```
aat att ttt gat gcc ggc gtt gct ggc gtt cca gat cct ata gct ggt       1440
Asn Ile Phe Asp Ala Gly Val Ala Gly Val Pro Asp Pro Ile Ala Gly
465                 470                 475                 480 gag ctt ccg gga gct gtt gtt gta ctt aag aaa gga aaa tct atg act       1488
Glu Leu Pro Gly Ala Val Val Val Leu Lys Lys Gly Lys Ser Met Thr
                485                 490                 495 gaa aaa gaa gta atg gat tac gtt gct agt caa gtt tca aat gca aaa       1536
Glu Lys Glu Val Met Asp Tyr Val Ala Ser Gln Val Ser Asn Ala Lys
            500                 505                 510 cgt ttg cgt ggt ggt gtc cgt ttt gtg gac gaa gta cct aaa ggt ctc       1584
Arg Leu Arg Gly Gly Val Arg Phe Val Asp Glu Val Pro Lys Gly Leu
        515                 520                 525 act ggt aaa att gac ggt aaa gca att aga gaa ata ctg aag aaa cca       1632
Thr Gly Lys Ile Asp Gly Lys Ala Ile Arg Glu Ile Leu Lys Lys Pro
    530                 535                 540 gtt gct aag atg                                                       1644
Val Ala Lys Met
545
```

<210> SEQ ID NO 6
<211> LENGTH: 548
<212> TYPE: PRT
<213> ORGANISM: Luciola lateralis

<400> SEQUENCE: 6

```
Met Glu Asn Met Glu Asn Asp Glu Asn Ile Val Tyr Gly Pro Glu Pro
1               5                   10                  15

Phe Tyr Pro Ile Glu Glu Gly Ser Ala Gly Ala Gln Leu Arg Lys Tyr
                20                  25                  30

Met Asp Arg Tyr Ala Lys Leu Gly Ala Ile Ala Phe Thr Asn Ala Leu
            35                  40                  45

Thr Gly Val Asp Tyr Thr Tyr Ala Glu Tyr Leu Glu Lys Ser Cys Cys
        50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
                100                 105                 110

Leu Arg Glu Leu Val His Ser Leu Gly Ile Ser Lys Pro Thr Ile Val
            115                 120                 125

Phe Ser Ser Lys Lys Gly Leu Asp Lys Val Ile Thr Val Gln Lys Thr
        130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Ile Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255
```

```
Tyr Leu Thr Cys Gly Phe Arg Ile Val Met Leu Thr Lys Phe Asp Glu
        260                 265                 270

Glu Thr Phe Leu Lys Thr Leu Gln Asp Tyr Lys Cys Ser Ser Val Ile
        275                 280                 285

Leu Val Pro Thr Leu Phe Ala Ile Leu Asn Arg Ser Glu Leu Leu Asp
        290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
                340                 345                 350

Ile Thr Pro Glu Gly Asp Asp Lys Pro Gly Ala Ser Gly Lys Val Val
                355                 360                 365

Pro Leu Phe Lys Ala Lys Val Ile Asp Leu Asp Thr Lys Lys Thr Leu
        370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
                405                 410                 415

Glu Gly Trp Leu His Thr Gly Asp Ile Gly Tyr Tyr Asp Glu Glu Lys
                420                 425                 430

His Phe Phe Ile Val Asp Arg Leu Lys Ser Leu Ile Lys Tyr Lys Gly
                435                 440                 445

Tyr Gln Val Pro Pro Ala Glu Leu Glu Ser Val Leu Leu Gln His Pro
        450                 455                 460

Asn Ile Phe Asp Ala Gly Val Ala Gly Val Pro Asp Pro Ile Ala Gly
465                 470                 475                 480

Glu Leu Pro Gly Ala Val Val Leu Lys Lys Gly Lys Ser Met Thr
                485                 490                 495

Glu Lys Glu Val Met Asp Tyr Val Ala Ser Gln Val Ser Asn Ala Lys
        500                 505                 510

Arg Leu Arg Gly Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
        530                 535                 540

Val Ala Lys Met
545
```

<210> SEQ ID NO 7
<211> LENGTH: 1644
<212> TYPE: DNA
<213> ORGANISM: Luciola lateralis
<220> FEATURE:
<221> NAME/KEY: CDS
<222> LOCATION: (1)..(1644)

<400> SEQUENCE: 7

```
atg gaa aac atg gag aac gat gaa aat att gtg tat ggt cct gaa cca      48
Met Glu Asn Met Glu Asn Asp Glu Asn Ile Val Tyr Gly Pro Glu Pro
1               5                  10                  15 ttt tac cct att gaa gag gga tct gct gga gca caa ttg cgc aag tat      96
Phe Tyr Pro Ile Glu Glu Gly Ser Ala Gly Ala Gln Leu Arg Lys Tyr
            20                  25                  30 atg gat cga tat gca aaa ctt gga gca att gct ttt act aac gca ctt     144
Met Asp Arg Tyr Ala Lys Leu Gly Ala Ile Ala Phe Thr Asn Ala Leu
        35                  40                  45
```

```
                                              -continued acc ggt gtc gat tat acg tac gcc gaa tac tta gaa aaa tca tgc tgt        192
Thr Gly Val Asp Tyr Thr Tyr Ala Glu Tyr Leu Glu Lys Ser Cys Cys
 50                  55                  60 cta gga gag gct tta aag aat tat ggt ttg gtt gtt gat gga aga att        240
Leu Gly Glu Ala Leu Lys Asn Tyr Gly Leu Val Val Asp Gly Arg Ile
 65                  70                  75                  80 gcg tta tgc agt gaa aac tgt gaa gaa ttc ttt att cct gta tta gcc        288
Ala Leu Cys Ser Glu Asn Cys Glu Glu Phe Phe Ile Pro Val Leu Ala
                     85                  90                  95 ggt tta ttt ata ggt gtc ggt gtg gct cca act aat gag att tac act        336
Gly Leu Phe Ile Gly Val Gly Val Ala Pro Thr Asn Glu Ile Tyr Thr
                100                 105                 110 cta cgt gaa ttg gtt cac agt tta ggc atc tct aag cca aca att gta        384
Leu Arg Glu Leu Val His Ser Leu Gly Ile Ser Lys Pro Thr Ile Val
            115                 120                 125 ttt agt tct aaa aaa gga tta gat aaa gtt ata act gta caa aaa acg        432
Phe Ser Ser Lys Lys Gly Leu Asp Lys Val Ile Thr Val Gln Lys Thr
130                 135                 140 gta act gct att aaa acc att gtt ata ttg gac agc aaa gtg gat tat        480
Val Thr Ala Ile Lys Thr Ile Val Ile Leu Asp Ser Lys Val Asp Tyr
145                 150                 155                 160 aga ggt tat caa tcc atg gac aac ttt att aaa aaa aac act cca caa        528
Arg Gly Tyr Gln Ser Met Asp Asn Phe Ile Lys Lys Asn Thr Pro Gln
                    165                 170                 175 ggt ttc aaa gga tca agt ttt aaa act gta gaa gtt aac cgc aaa gaa        576
Gly Phe Lys Gly Ser Ser Phe Lys Thr Val Glu Val Asn Arg Lys Glu
                180                 185                 190 caa gtt gct ctt ata atg aac tct tcg ggt tca acc ggt ttg cca aaa        624
Gln Val Ala Leu Ile Met Asn Ser Ser Gly Ser Thr Gly Leu Pro Lys
            195                 200                 205 ggt gtg caa ctt act cat gaa aat gca gtc act aga ttt tct cac gct        672
Gly Val Gln Leu Thr His Glu Asn Ala Val Thr Arg Phe Ser His Ala
210                 215                 220 aga gat cca att tat gga aac caa gtt tca cca ggc acg gct att tta        720
Arg Asp Pro Ile Tyr Gly Asn Gln Val Ser Pro Gly Thr Ala Ile Leu
225                 230                 235                 240 act gta gta cca ttc cat cat ggt ttt ggt atg ttt act act tta ggc        768
Thr Val Val Pro Phe His His Gly Phe Gly Met Phe Thr Thr Leu Gly
                    245                 250                 255 tat cta act tgt ggt ttt cgt att gtc atg tta acg aaa ttt gac gaa        816
Tyr Leu Thr Cys Gly Phe Arg Ile Val Met Leu Thr Lys Phe Asp Glu
                260                 265                 270 gag act ttt tta aaa aca ctg caa gat tac aaa tgt tca agc gtt att        864
Glu Thr Phe Leu Lys Thr Leu Gln Asp Tyr Lys Cys Ser Ser Val Ile
            275                 280                 285 ctt gta ccg act ttg ttt gca att ctt aat aga agt gaa tta ctc gat        912
Leu Val Pro Thr Leu Phe Ala Ile Leu Asn Arg Ser Glu Leu Leu Asp
290                 295                 300 aaa tat gat tta tca aat tta gtt gaa att gca tct ggc gga gca cct        960
Lys Tyr Asp Leu Ser Asn Leu Val Glu Ile Ala Ser Gly Gly Ala Pro
305                 310                 315                 320 tta tct aaa gaa att ggt gaa gct gtt gct aga cgt ttt aat tta ccg       1008
Leu Ser Lys Glu Ile Gly Glu Ala Val Ala Arg Arg Phe Asn Leu Pro
                    325                 330                 335 ggt gtt cgt caa ggc tat ggt tta aca gaa aca acc tct gca att att       1056
Gly Val Arg Gln Gly Tyr Gly Leu Thr Glu Thr Thr Ser Ala Ile Ile
                340                 345                 350 atc aca ccg gaa ggc gat gat aaa cca ggt gct tct ggc aaa gtt gtg       1104
Ile Thr Pro Glu Gly Asp Asp Lys Pro Gly Ala Ser Gly Lys Val Val
            355                 360                 365
```

```
cca tta ttt aaa gca aaa gtt atc gat ctt gat act aaa aaa act ttg    1152
Pro Leu Phe Lys Ala Lys Val Ile Asp Leu Asp Thr Lys Lys Thr Leu
    370                 375                 380 ggc ccg aac aga cgt gga gaa gtt tgt gta aag ggt cct atg ctt atg    1200
Gly Pro Asn Arg Arg Gly Glu Val Cys Val Lys Gly Pro Met Leu Met
385                 390                 395                 400 aaa ggt tat gta gat aat cca gaa gca aca aga gaa atc ata gat gaa    1248
Lys Gly Tyr Val Asp Asn Pro Glu Ala Thr Arg Glu Ile Ile Asp Glu
                405                 410                 415 gaa ggt tgg ttg cac aca gga gat att ggg tat tac gat gaa gaa aaa    1296
Glu Gly Trp Leu His Thr Gly Asp Ile Gly Tyr Tyr Asp Glu Glu Lys
            420                 425                 430 cat ttc ttt atc gtg gat cgt ttg aag tct tta atc aaa tac aaa gga    1344
His Phe Phe Ile Val Asp Arg Leu Lys Ser Leu Ile Lys Tyr Lys Gly
        435                 440                 445 tat caa gta cca cct gct gaa tta gaa tct gtt ctt ttg caa cat cca    1392
Tyr Gln Val Pro Pro Ala Glu Leu Glu Ser Val Leu Leu Gln His Pro
    450                 455                 460 aat att ttt gat gcc ggc gtt gct ggc gtt cca gat cct ata gct ggt    1440
Asn Ile Phe Asp Ala Gly Val Ala Gly Val Pro Asp Pro Ile Ala Gly
465                 470                 475                 480 gag ctt ccg gga gct gtt gtt gta ctt gaa aaa gga aaa tct atg act    1488
Glu Leu Pro Gly Ala Val Val Val Leu Glu Lys Gly Lys Ser Met Thr
                485                 490                 495 gaa aaa gaa gta atg gat tac gtt gct agt caa gtt tca aat gca aaa    1536
Glu Lys Glu Val Met Asp Tyr Val Ala Ser Gln Val Ser Asn Ala Lys
            500                 505                 510 cgt ttg cgt ggt ggt gtc cgt ttt gtg gac gaa gta cct aaa ggt ctc    1584
Arg Leu Arg Gly Gly Val Arg Phe Val Asp Glu Val Pro Lys Gly Leu
        515                 520                 525 act ggt aaa att gac ggt aaa gca att aga gaa ata ctg aag aaa cca    1632
Thr Gly Lys Ile Asp Gly Lys Ala Ile Arg Glu Ile Leu Lys Lys Pro
    530                 535                 540 gtt gct aag atg                                                    1644
Val Ala Lys Met
545
```

<210> SEQ ID NO 8
<211> LENGTH: 548
<212> TYPE: PRT
<213> ORGANISM: Luciola lateralis

<400> SEQUENCE: 8

```
Met Glu Asn Met Glu Asn Asp Glu Asn Ile Val Tyr Gly Pro Glu Pro
1               5                   10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125
```

-continued

```
Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
                180                 185                 190

Gln Val Ala Leu Ile Met Asn Ser Ser Gly Ser Thr Gly Leu Pro Lys
                195                 200                 205

Gly Val Gln Leu Thr His Glu Asn Ala Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
                260                 265                 270

Glu Thr Phe Leu Lys Thr Leu Gln Asp Tyr Lys Cys Ser Ser Val Ile
    275                 280                 285

Leu Val Pro Thr Leu Phe Ala Ile Leu Asn Arg Ser Glu Leu Leu Asp
290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
                340                 345                 350

Ile Thr Pro Glu Gly Asp Asp Lys Pro Gly Ala Ser Gly Lys Val Val
    355                 360                 365

Pro Leu Phe Lys Ala Lys Val Ile Asp Leu Asp Thr Lys Lys Thr Leu
370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
                405                 410                 415

Glu Gly Trp Leu His Thr Gly Asp Ile Gly Tyr Tyr Asp Glu Glu Lys
                420                 425                 430

His Phe Phe Ile Val Asp Arg Leu Lys Ser Leu Ile Lys Tyr Lys Gly
    435                 440                 445

Tyr Gln Val Pro Pro Ala Glu Leu Glu Ser Val Leu Leu Gln His Pro
450                 455                 460

Asn Ile Phe Asp Ala Gly Val Ala Gly Val Pro Asp Pro Ile Ala Gly
465                 470                 475                 480

Glu Leu Pro Gly Ala Val Val Val Leu Glu Lys Gly Lys Ser Met Thr
                485                 490                 495

Glu Lys Glu Val Met Asp Tyr Val Ala Ser Gln Val Ser Asn Ala Lys
                500                 505                 510

Arg Leu Arg Gly Gly Val Arg Phe Val Asp Glu Val Pro Lys Gly Leu
    515                 520                 525
```

```
Thr Gly Lys Ile Asp Gly Lys Ala Ile Arg Glu Ile Leu Lys Lys Pro
    530             535             540

Val Ala Lys Met
545
```